United States Patent [19]

Warriner

[11] Plant 4,847

[45] May 18, 1982

[54] ROSE PLANT JP 76-5492

[75] Inventor: William A. Warriner, Tustin, Calif.

[73] Assignee: Jackson & Perkins Company, Medford, Oreg.

[21] Appl. No.: 190,025

[22] Filed: Sep. 23, 1980

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having yellow blooms on long, straight stems, with glossy, mildew resistant foliage, and mild fragrance.

1 Drawing Figure

This present invention relates to a new and distinct variety of rose plant of the hybrid tea class which was originated by me by crossing an unnamed variety, with the variety Sunshine, U.S. Plant Pat. No. 3,791.

The primary objective of this breeding was to produce a new rose variety suitable for the production of cut blooms when grown in a greenhouse, producing yellow blooms. This objective was substantially achieved along with other desirable improvements as evidenced by the following unique combination of characteristics which are outstanding in the new variety and which distinguish it from its parents as well as from all other varieties of which I am aware:

1. A vigorous, upright plant producing straight stems of 18" to 24" length.
2. Pointed yellow buds opening to high centered blooms, fading only slightly in three or four days.
3. Glossy, mildew resistant foliage.
4. Mild fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Unnamed variety.

*Pollen parent.*—Sunshine, U.S. Plant Pat. No. 3,791.

Classification:

*Botanical.*—Rosa hybrid.

*Commercial.*—Hybrid tea.

FLOWER

Observations made from specimens grown in a greenhouse in Irvine, Calif. during September, 1980.

Blooming habit: Continuous.

Bud:

*Size.*—1¼" when petals start to unfurl.

*Form.*—Pointed ovoid.

*Color.*—When sepals first divide, Yellow 13A to 13D. When half blown; upper side of petals, Yellow, near 13A; lower side of petals, Yellow, near 13A.

*Sepals.*—Color: outer surface, Green 138A. Three appendaged sepals lightly appendaged. Edges with stipitate glands. Two unappendaged sepals hairy edged, no glands.

*Receptacle.*—Color: Green 138A. Shape: funnel. Size: large, broad. Surface: smooth.

*Peduncle.*—Length: long. Surface: glandular. Color: light green. Strength: stiff, erect.

Bloom:

*Size.*—Large. Average open size is 4 inches.

*Borne.*—Single.

*Stems.*—Long, strong.

*Form.*—When first open, high centered. Permanence: outer petal edges slightly curled.

*petalage.*—Number of petals under normal conditions, 30.

*Color.*—Center of flower: upper side of petals, Yellow, near 13A; reverse side of petals, Yellow 13A; base of petals, Yellow 13A. General tonality from a distance, Yellow, 13A.

*Variegations.*—Occasional green streaks on outside petals.

*Discoloration.*—General tonality at end of first day, Yellow 13B; third day, Yellow 13C to 13D.

*Fragrance.*—Moderate.

Petals:

*Texture.*—Thick.

*Shape.*—Round.

*Form.*—Tips slightly recurved.

*Arrangement.*—Irregular. Petaloids in center, few.

*Persistence.*—Drop off cleanly.

*Lastingness.*—On the plant, long. As cut flower, long.

Reproductive parts:

*Anthers.*—Large, many. Color: yellow. Arrangement: regular around styles.

*Filaments.*—Color: reddish.

*Pollen.*—Lemon yellow.

*Styles.*—Color: yellow.

*Stigmas.*—Color: yellow.

PLANT

Form: Bush.

Growth: Vigorous, upright.

Foliage: Number of leaflets on normal mid-stem leaves, 5 or 7.

*Size.*—Large.

*Quantity.*—Normal.

*Color.*—New foliage: light green, overlayed lightly with a color near Grayed Purple 183D. Old foliage: Green 137A.

Leaflets:

*Shape.*—Oval pointed.

*Texture.*—Upper side, glossy.

*Edge.*—Serrated.

*Serration.*—Single, small.

*Petiole.*—Rachis, color: green. Underside: prickles.

*Stipules.*—Long, edges glandular.

*Disease resistance.*—Resistant to mildew under normal growing conditions at Irvine, Calif.

Wood:

*New wood.*—Color: light green. Bark: smooth.

*Old wood.*—Color: green. Bark: smooth.

Prickles:

*Quantity.*—On main stalks from base, ordinary. On laterals from stalks, ordinary.

*Form.*—Long base, long, hooked downward.

*Color when young.*—Green.

*Position.*—Irregular.

Small prickles:

*Quantity.*—On main stalks, none. On laterials, none.

I claim:

1. A new and distinct variety of rose plant of the hybrid tea class, substantially as herein shown and described, characterized particularly as to novelty by the unique combination of its long straight stems, glossy foliage, yellow buds and blooms with a moderate fragrance.

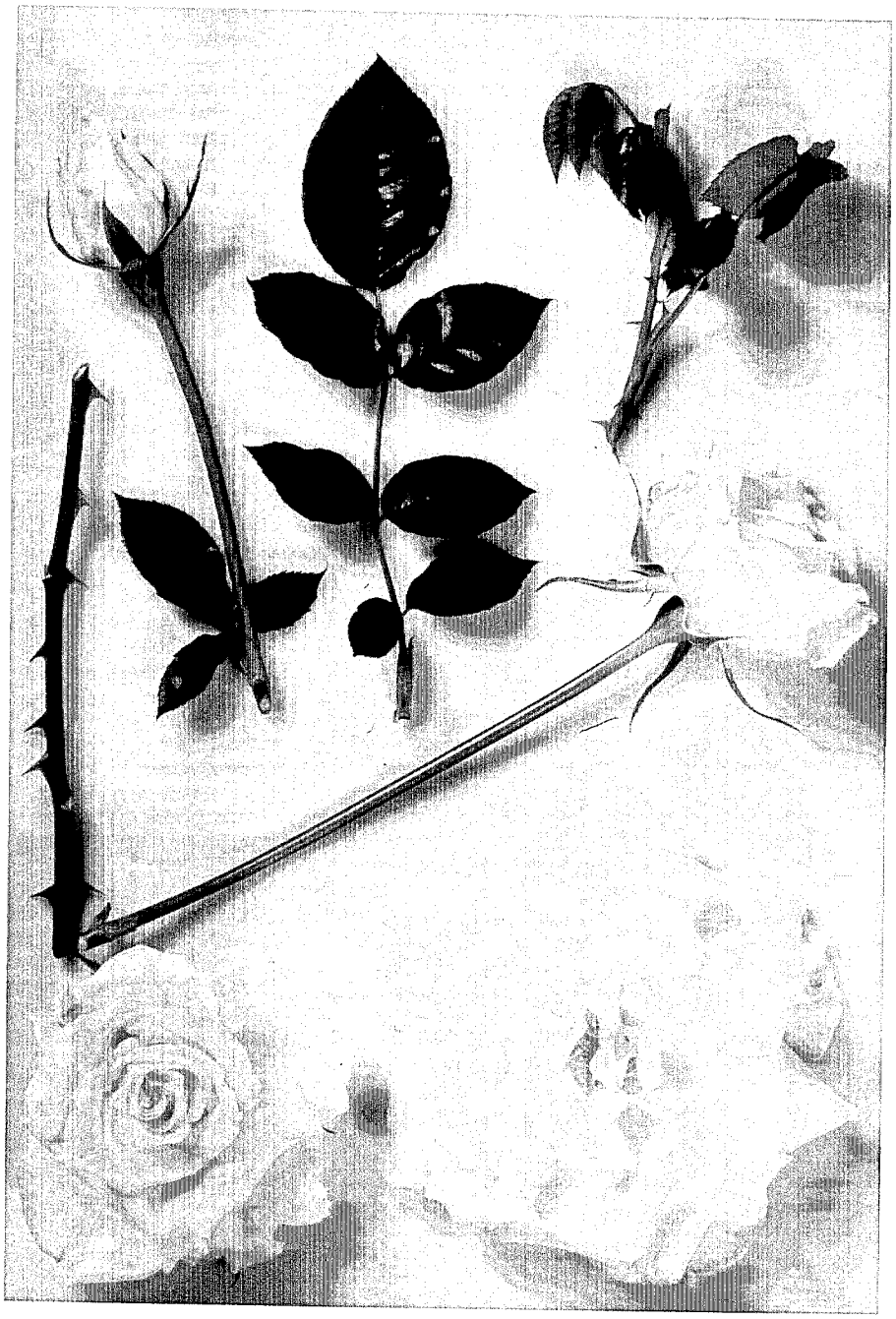

* * * * *